United States Patent [19]

Greenberg et al.

[11] Patent Number: 4,581,984
[45] Date of Patent: Apr. 15, 1986

[54] APPARATUS FOR MEASURING HUMAN RESPIRATION

[75] Inventors: Mishel Greenberg, New Hyde Park, N.Y.; William H. Smyers, Jr., Wethersfield, Conn.; Milton Chernack, New York, N.Y.

[73] Assignee: Chesebrough-Pond's Inc., Greenwich, Conn.

[21] Appl. No.: 643,461

[22] Filed: Aug. 23, 1984

Related U.S. Application Data

[62] Division of Ser. No. 375,298, May 5, 1982, Pat. No. 4,499,905.

[51] Int. Cl.$^4$ .................................................. F16J 9/00
[52] U.S. Cl. ............................................. 92/240; 92/250
[58] Field of Search ................. 92/240, 250, 241–246, 92/251, 252, 257; 277/212 F, 215

[56] References Cited

U.S. PATENT DOCUMENTS

| | | | |
|---|---|---|---|
| 1,478,561 | 12/1923 | Faessel | 277/212 F |
| 1,900,414 | 3/1933 | Ellberg et al. | |
| 3,068,703 | 12/1962 | Morton | 73/419 |
| 3,523,001 | 8/1970 | Sylvester et al. | 92/240 X |

FOREIGN PATENT DOCUMENTS

123351 2/1919 United Kingdom ................ 92/240

Primary Examiner—Edward K. Look
Attorney, Agent, or Firm—Morgan, Finnegan, Pine, Foley & Lee

[57] ABSTRACT

A lightweight and portable volumetric spirometer for measuring the volume of and rate of flow of air inhaled by human lungs. The device includes a movable piston within a first transparent cylindrical chamber provided with calibrated markings along its surface for measuring the volume of air withdrawn from the chamber. The first chamber communicates with a breathing tube assembly through which the user inhales. The breathing tube assembly is uniquely adapted so that the inhaled air flow is divided into two fixed portions, one portion of which comes from the chamber, the other portion of which comes from a second chamber communicating with the outside atmosphere. As air is inhaled, the piston rises to a height that can be related to the total volume inhaled. Preferably, there is a counterweight in the second chamber which also rises during inhalation to counterbalance the resistance to movement of the piston and which gives an indication of the rate of inhalation.

2 Claims, 15 Drawing Figures

APPARATUS FOR MEASURING HUMAN RESPIRATION

This is a division of application Ser. No. 375,298, filed May 5, 1982, now U.S. Pat No. 4,499,905.

BACKGROUND OF THE INVENTION

This invention relates to an apparatus for the measuring of human respiration. More particularly, it relates to a device for measuring the volume of air entering human lungs.

There are known in the art devices for human respiratory exercise or for the practice of breath control. Devices of these types are disclosed, for example, in Tunbull, U.S. Pat. No. 3,811,671, Russo, U.S. Pat. No. 4,086,918, Hanson, U.S. Pat. No. 3,695,608 and Russo, U.S. Pat. No. 4,060,074. Such devices typically involve the exhalation of air into, or inhalation of air from an enclosed chamber.

Also known are instruments for the purpose of measuring the amount of air entering or leaving human lungs. Such instruments are sometimes referred to as spirometers. Particular examples are disclosed in McMillan, U.S. Pat. No. 3,722,506, Rand, et al., U.S. Pat. No. 3,635,214 and Ruskin, et al., U.S. Pat. No. 3,826,247.

Many spirometer devices are costly and cumbersome. Although newer, more portable instruments are now available, there remains a need for volumetric spirometers which are accurate and reliable, yet relatively inexpensive and easily transportable.

OBJECTS OF THE INVENTION

With the foregoing in mind, it is an object of this invention to provide a device for measuring the amount of air inhaled by human lungs.

It is another object of this invention to provide for the measuring or testing human breathing capacity by means of a device which is, in addition to being accurate and reliable, readily portable, lightweight and durable.

It is a further object of this invention to provide a new and improved inhalation device which provides an indication of measurement of a relatively large volume of air with a relatively compact device.

A further object of this invention is to provide a compact inhalation device indicating the rate of and amount of inhalation.

A further object of this invention is to provide an inhalation device having a first means for indicating the volume inhaled and a second means for indicating the rate of inhalation.

Another object of this invention is to provide an inhalation device having first and second chambers in fluid communication with an inhalation conduit through openings having a predetermined ratio of the relative size of the openings.

A still further object of this invention is to provide an inhalation device having at least two chambers in fluid communication with an inhalation conduit whereby upon inhalation a major portion of air is inhaled through a chamber in communication with atmosphere and wherein a minor portion of air comes from another chamber having means therein indicating the total amount of air inhaled.

A still further object of the invention is to provide an inhalation device having at least two chambers in communication with an inhalation tube at least one chamber having a movable piston assembly and there being a counterweight which counteracts the frictional forces encountered by the piston assembly.

Still another object of this invention is to provide an inhalation device having a piston assembly movable in one chamber and counterweight means which counterbalance frictional resistance to the piston assembly which varies depending on the rate of inhalation.

Another object of this invention is to provide an inhalation device having a movable piston means in a chamber and a unique sealing arrangement between the piston means and the chamber.

Additional objects and advantages of the invention will be set forth in the description which follows and, in part, will be obvious from the description, the objects and advantages being realized and obtained by means of the parts, instrumentation, methods, apparatus and procedures particularly pointed out in the appended claims.

BRIEF DESCRIPTION OF THE INVENTION

Briefly described, the invention comprises the following chief elements or parts:

a first hollow cylindrical chamber having a piston suitably positioned and adapted to be movable therein, the chamber being vented to the atmosphere;

a second hollow chamber preferably having a counterweight positioned therein, the chamber being open to atmosphere;

an inhalation tube assembly in open communication with the first and second hollow chamber which forms a flow passageway terminating with a mouthpiece through which a patient can inhale and cause the piston to move.

The relationship between the inhalation tube assembly and the first and second chambers is such that a major portion of the inhaled air comes from the atmosphere through the second chamber and a minor portion from the first chamber in a predeter- mined manner so that a large volume of air can be inhaled with a relatively compact device. The first chamber includes a piston assembly which indicates the volume of air inhaled by its position within the chamber.

A feature of the invention is the dividing of or predetermined proportioning of the air flow to the user such that a fixed proportion of the total flow comes from the chamber containing the movable piston which functions as the volume measuring chamber as will be explained more fully below. This division of the air flow is accomplished by means of two ports, one leading to the piston containing chamber and the other leading to the other chamber which in turn communicates with the atmosphere. Preferably the port leading to the atmosphere has a considerably larger area, so that when the user inhales through the inhalation tube most of the air flow comes through the larger port, and only a small portion comes from the volume measuring chamber through the smaller port. As air above the piston is removed by inhalation, the piston rises to a height that can be related to the total volume inhaled. This arrangement is desirable since it permits the use of a relatively small inhalation device. Were it not for this arrangement, it would be necessary for a relatively large device to be used in view of the volume of air desired to be inhaled.

Because the piston has weight and friction, it slows down the air flow from the volume measuring chamber. To compensate for this resistance, in the preferred embodiment a counterweight is included in the device to add an equivalent or nearly equivalent amount of drag to the air flow through the larger port in the breathing tube assembly. The counterweight is constructed and arranged to take into account the effect of the frictional drag forces on the amount of air being inhaled.

This invention consists of the novel parts, steps, constructions and improvements shown and described herein.

The accompanying drawings which are incorporated in and constitute part of the specification illustrate an embodiment of the invention and, together with the description, serve to explain the principles of the invention.

DETAILED DESCRIPTION OF INVENTION

Figure 1:
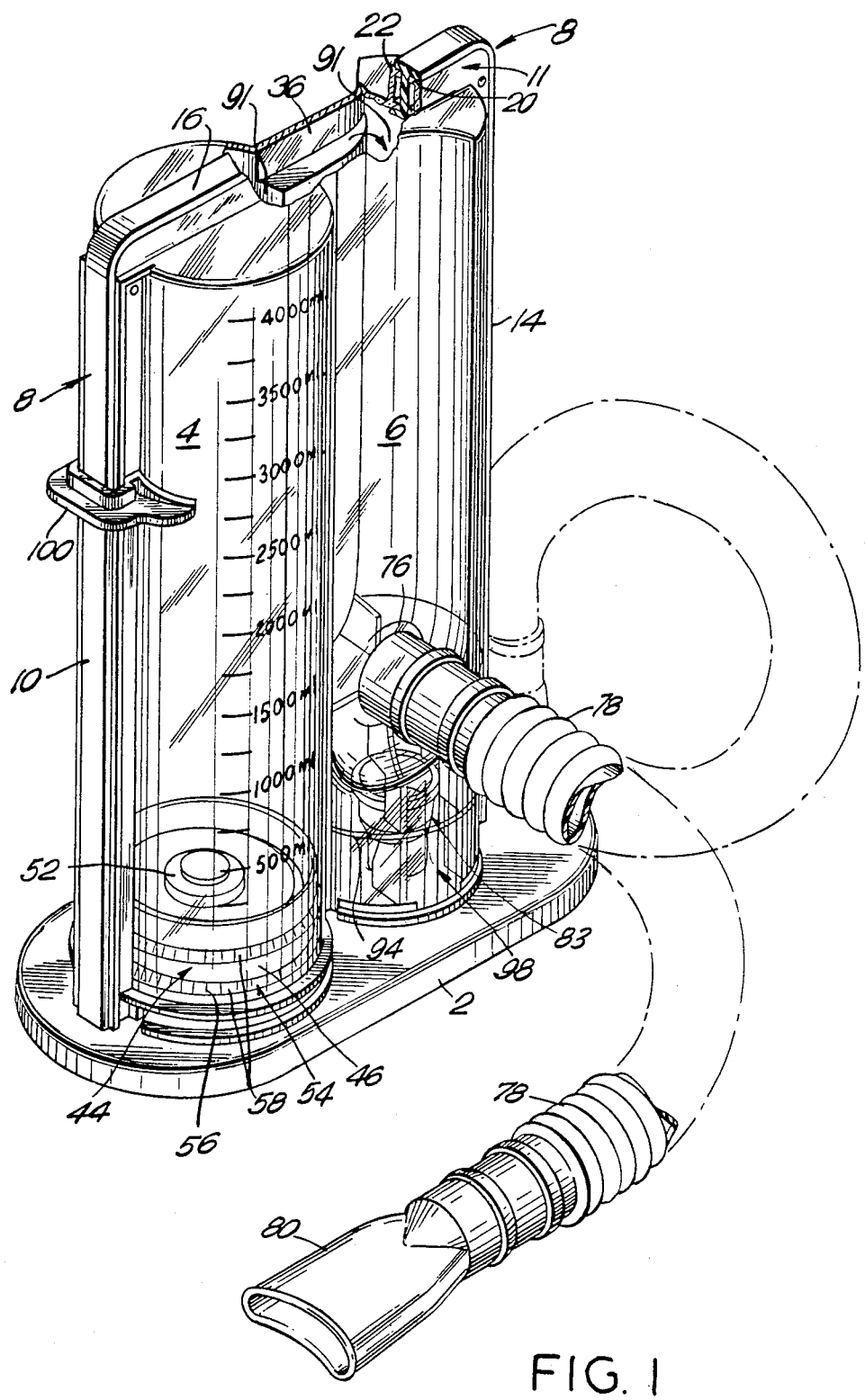
FIG. 1 is a perspective view of a spirometer in accordance with the invention.

Referrring to the drawings, a preferred embodiment of the invention is illustrated.

As embodied, the invention includes a base 2 on which the inhalation structure is mounted. The base 2, in addition to serving as a base, can also function as a stand to maintain the inhalation unit or structure in an upright position. A pair of upright or vertical columns 4 and 6 are mounted on the base 2 in any convenient manner. The vertical columns 4 and 6 consist of a two-piece molded construction (See FIG. 2) wherein the pieces are brought together in a sealed relationship by the frame shown generally at 8.

The entire apparatus, including all functioning and movable parts, can be constructed of a lightweight molded plastic as will be explained subsequently.

The interior wall of the vertical column 4 is at least in part, preferably frosted to reduce the surface area and to reduce resistance to the subsequently described piston.

The frame 8 has three vertical legs 10, 12, and 14 and a connecting horizontal leg 16. As will be explained, the frame 8 is used to assemble in sealed relationship the parts 9 and 11 which when assembled form the vertical columns 4 and 6 and associated structure.

Figure 2:
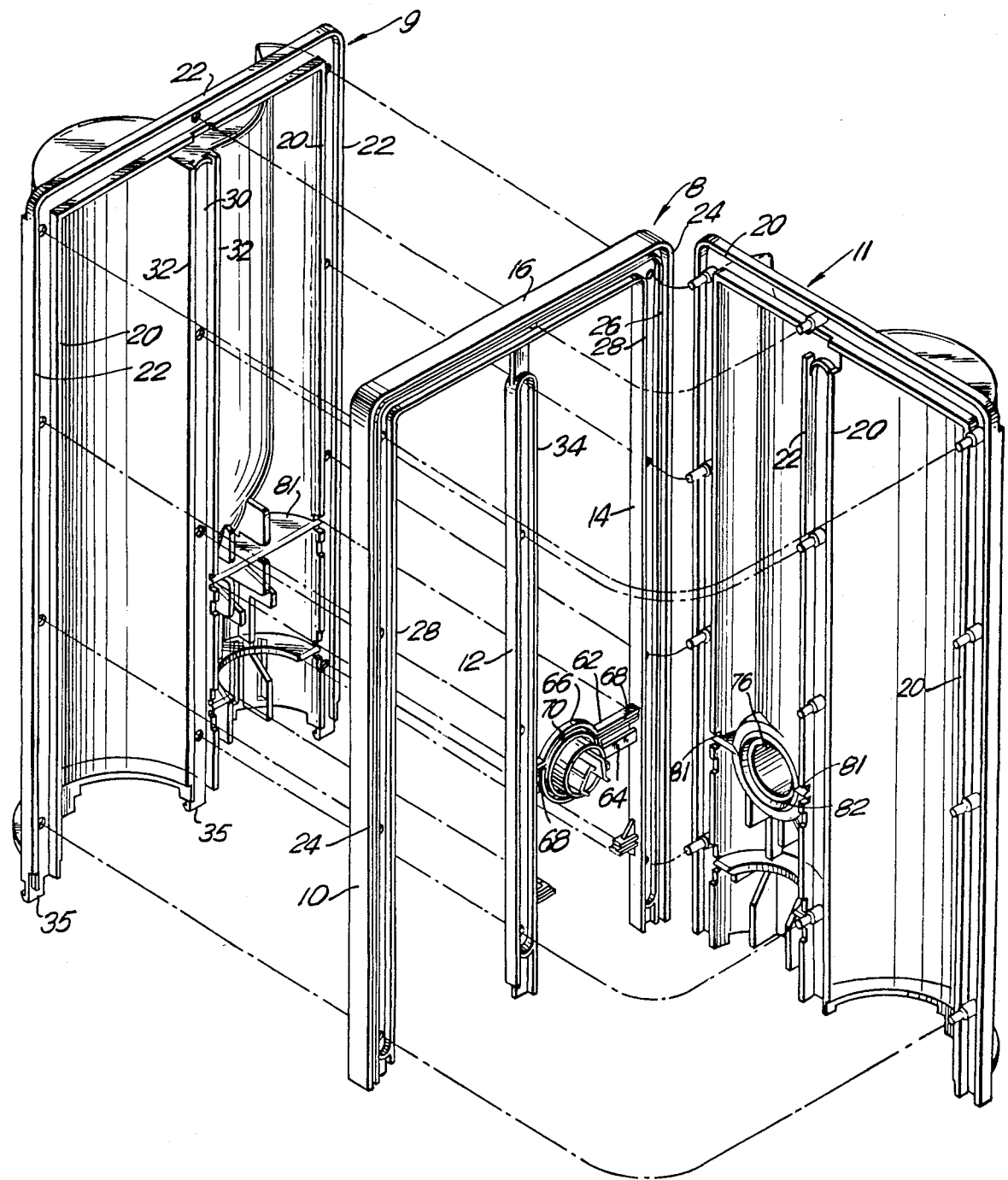
FIG. 2 is an exploded view of the spirometer of FIG. 1 before assembly.
Figure 3:
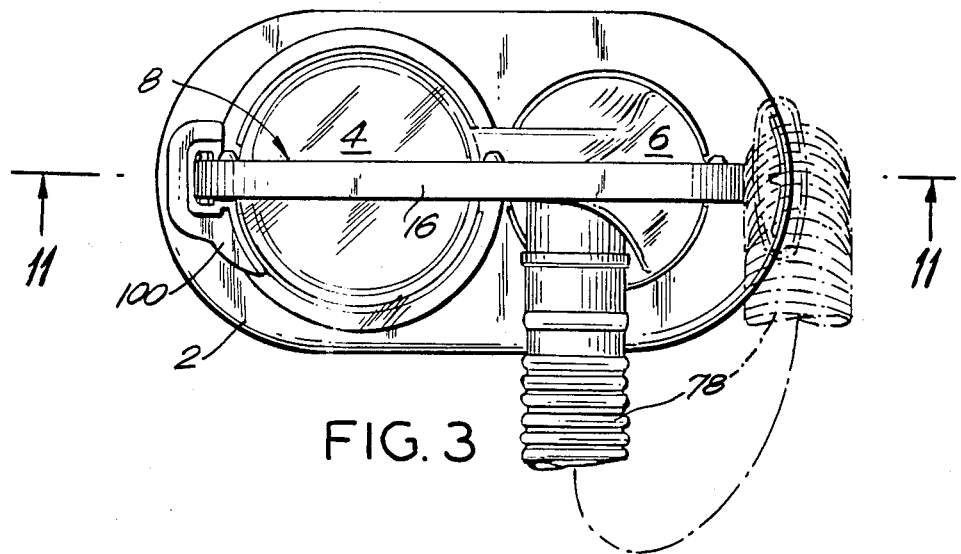
FIG. 3 is a top plan view of the spirometer of FIG. 1.
Figure 4:
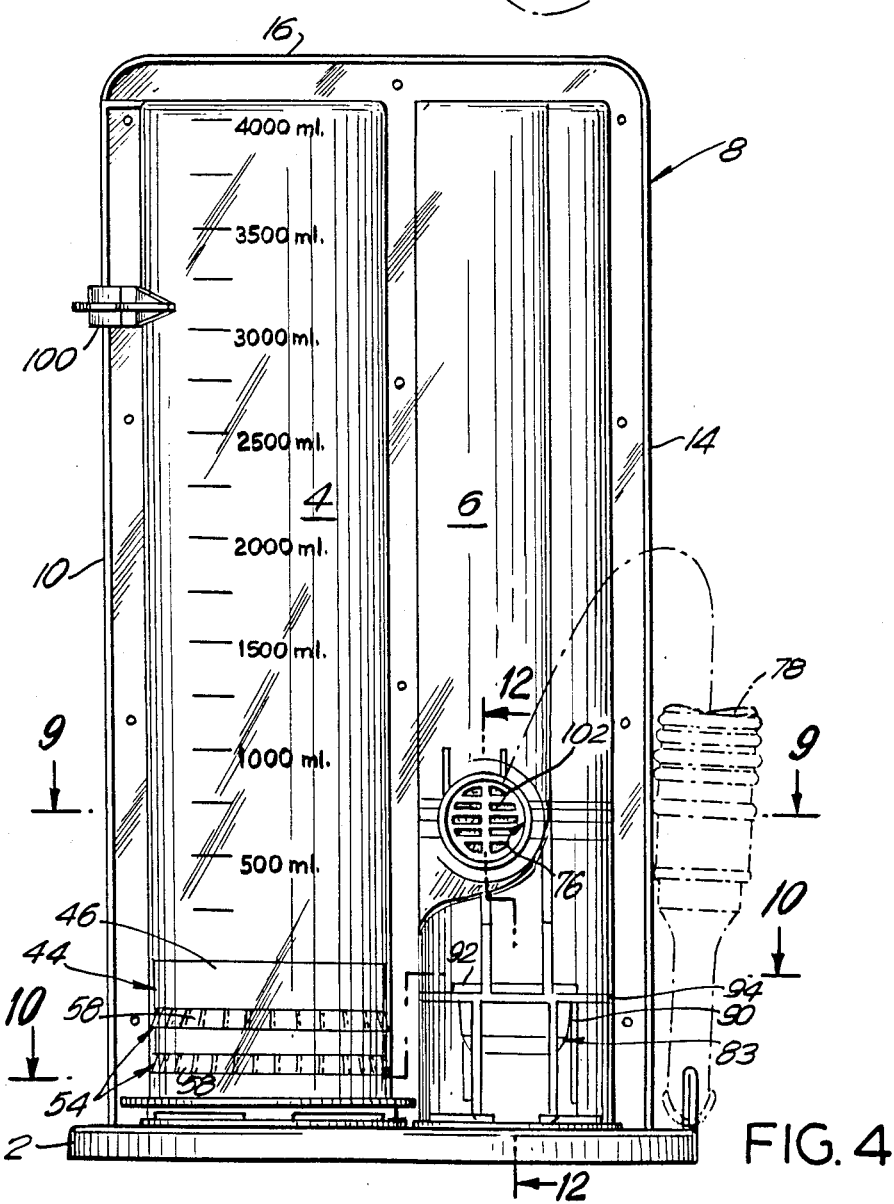
FIG. 4 is a front elevational view of the spirometer of FIG. 1, with the mouthpiece assembly in the rest position.
Figure 9:
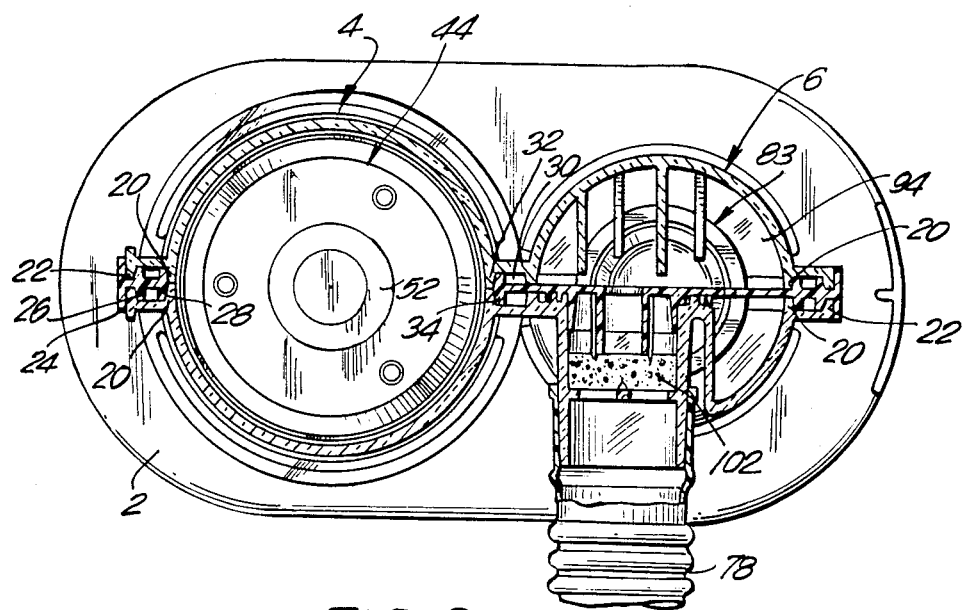
FIG. 9 is a sectional view of the spirometer along line 9—9 indicated in FIG. 4.
Figure 10:
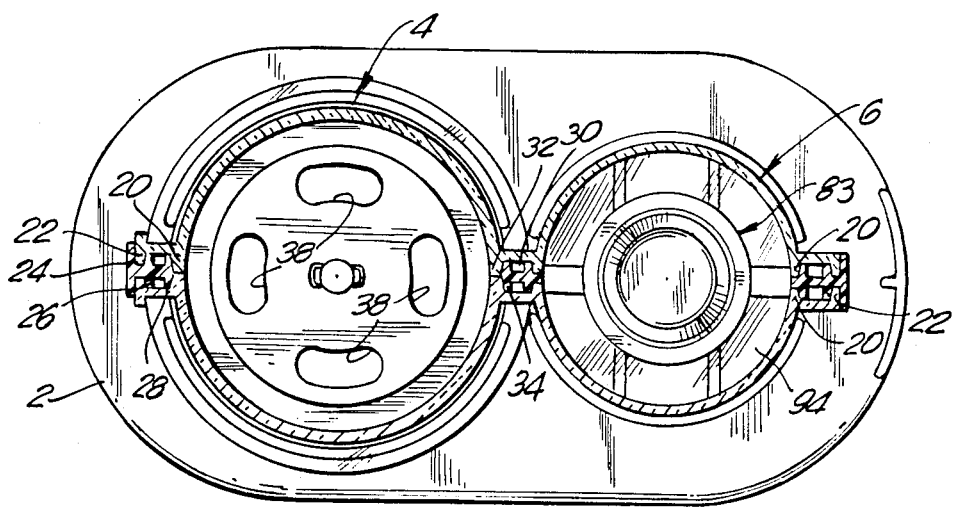
FIG. 10 is a sectional view of the spirometer along line 10—10 indicated in FIG. 4.

As can be seen in FIGS. 2, 9 and 10, the portions which form columns 4 and 6 include flanges 20 which extend from the column portions and spaced therefrom are flanges 22 forming a space therebetween. The legs 10, 14 and 16 of the frame 8 include three spaced apart flanges 24, 26 and 28 (See FIG. 2).

As embodied, the flanges 22 on the columns 4 and 6 fit between flanges 24 and 26 on the outer legs 10 and 14 while flange 28 is in sealing relationship with flange 20. The inner or adjacent portions of columns 4 and 6 include recesses 30 formed by flanges 32. The inner or center leg 12 of the frame 8 includes pairs of flanges 34 which extend into the recesses 30 and into sealing engagement with the spaced apart flanges 32 which form the recesses 30.

The lower ends of the columns 4 and 6 include tabs 35 (FIG. 2) or the like adapted to fit within appropriate openings in the base to form a unitary structure.

Figure 7:
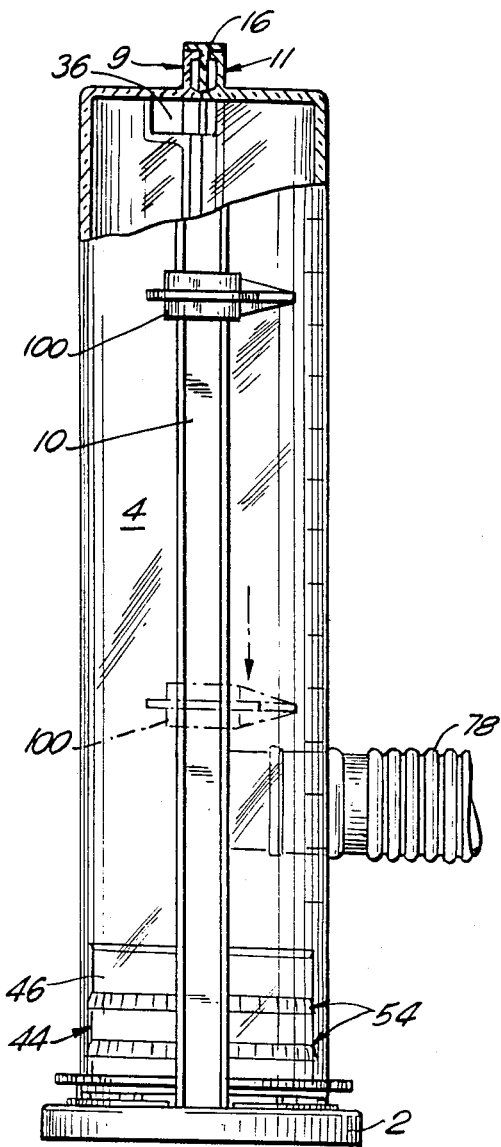
FIG. 7 is an elevational view from the left side of the spirometer of FIG. 1.
Figure 8:
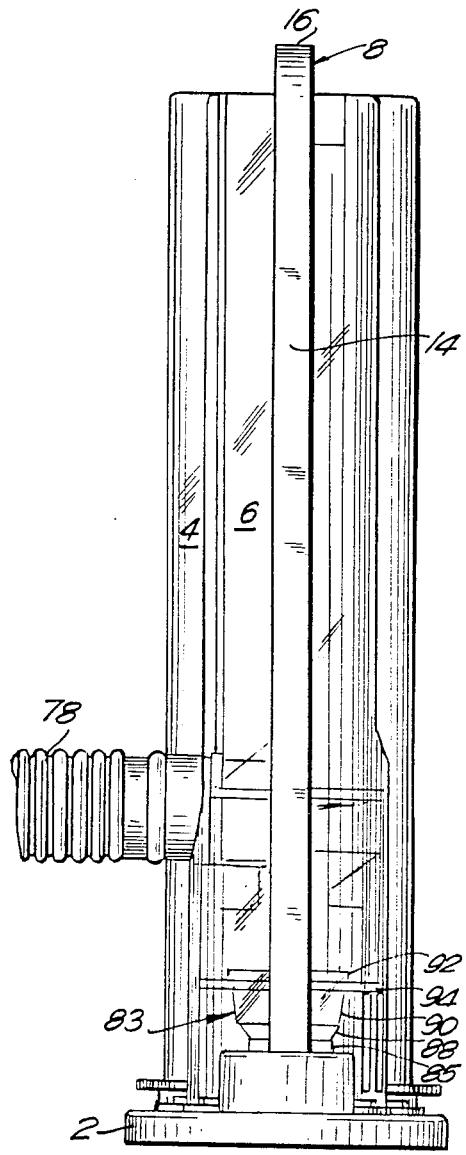
FIG. 8 is an elevational view from the right side of the spirometer of FIG. 1.
Figure 11:
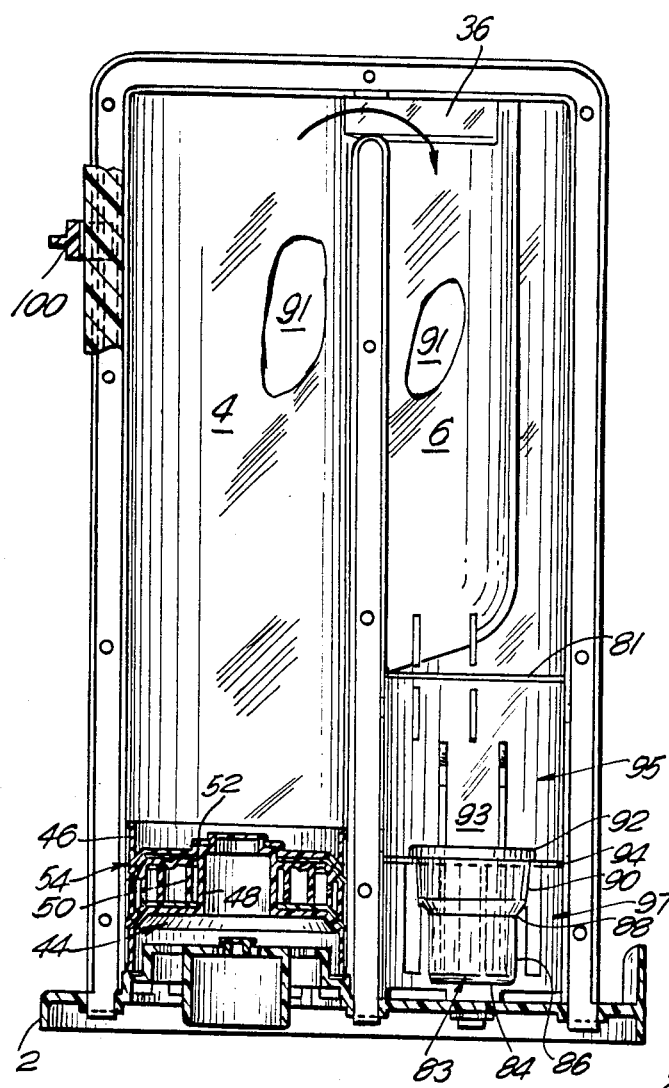
FIG. 11 is a cross-sectional view of the spirometer along line 11—11 indicated in FIG. 3.

The columns 4 and 6, as can be seen in FIGS. 1, 7 and 11 are in fluid communication by virtue of passageway 36 extending between the columns 4 and 6. The column 4 is cylindrical in shape whereas column 6 is somewhat triangular in cross section over a substantial length. The lower most portion of column 6 is also cylindrical in form. Vertical column 4 is open to the atmosphere by virtue of a series of openings or aperture 38 in the base as can be seen in FIG. 10.

Figure 6:
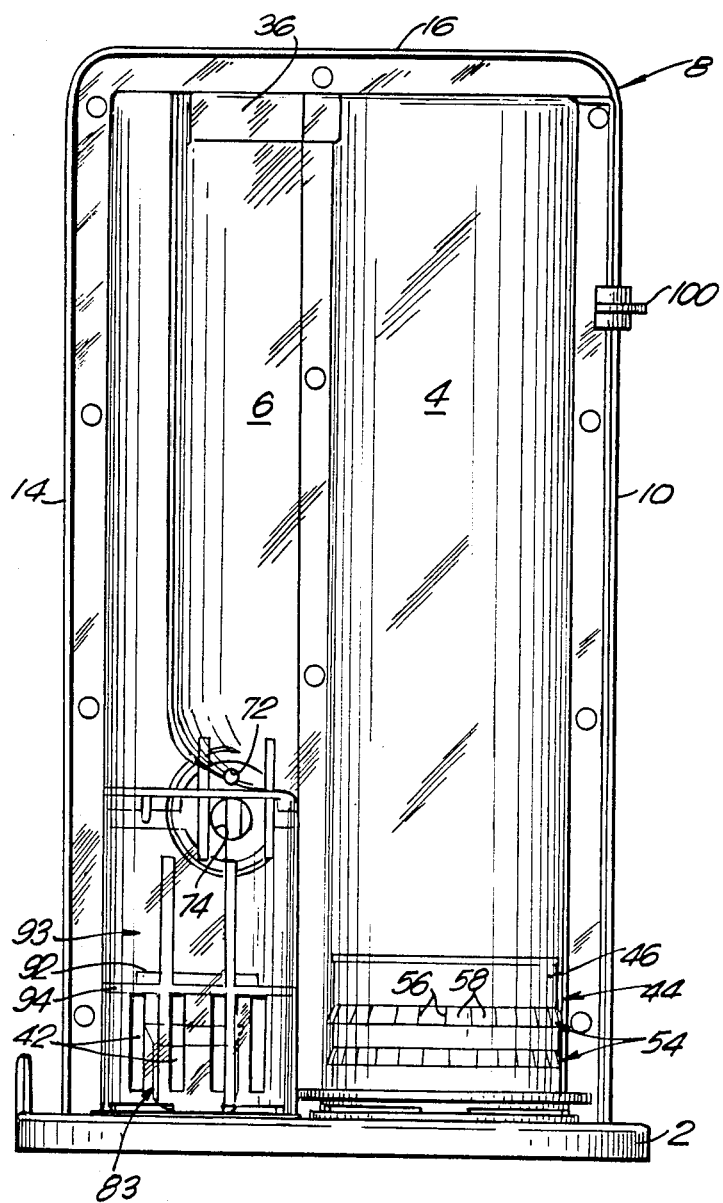
FIG. 6 is a front elevational view of the spirometer of FIG. 1, from the reverse side shown in FIG. 4.

The bottom portion of the other vertical column 6 is also open to the atmosphere by virtue of a series of vertical openings 42 positioned at the rear of column 6. (FIG. 6).

In accordance with this invention means is provided for positioning a vertically movable piston in sealed relationship within one of the vertical columns.

As embodied, this means includes a piston assembly 44 (FIGS. 1 and 13-14) which is slidably mounted within the vertical cylindrical column 4. As heretofore indicated, the position of the piston also serves as an indicator of the volume of inhaled air.

The piston assembly consists of a base member 46 having a centrally located stud 48 extending upwardly. Mounted on the stud 48 is an intermediate piston part 50 and a top piston part 52. These piston assembly parts are cylindrical in form and have a diameter which is slightly less than the diameter of vertical column 4 so that the piston assembly can slide freely within the vertical column 4.

Figure 13:
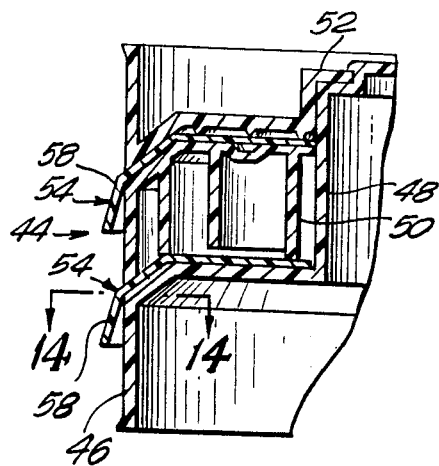
FIG. 13 is a partial sectional view of the piston assembly.

The intermediate and top piston parts are nested as shown in FIG. 13.

In accordance with this invention, means is provided for preventing leakage between the piston assembly and the vertical column 4 so that there is a sealed relationship between the piston assembly and the vertical column 4.

As embodied, this means includes a relatively thin gauge film made of ethylene vinyl acetate or polyethylene film which is part of the piston assembly and this means includes a portion which engages the wall of the column 4 to form a seal between the piston assembly and the vertical column 4.

As embodied, the thin, flexible film-like disk 54 has an aperture which fits over the stud 48 and extends radially outwardly so as to extend beyond the outer surface of the piston assembly. The thin, flexible disk 54 is radially slitted 56 from its periphery (FIG. 15) inwardly so as to form a plurality of flaps 58.

Figure 14:
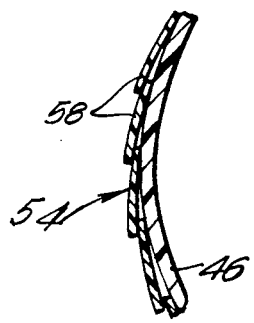
FIG. 14 is a sectional view taken along line 14—14 of FIG. 13.

As can be seen, in FIG. 13, the radial ends of the piston assembly parts 46, 50, and 52 are sloped downwardly so that the radially terminal ends of the flaps 58 are also sloped downwardly. The downward slope reduces the diameter of the disk causing flaps 58 to overlap (FIG. 14).

As can be seen from the drawings, there are two such thin disk-like films positioned between the parts of the piston assembly. The invention, however, is not limited to any particular number of such film-like disks.

Figure 15:
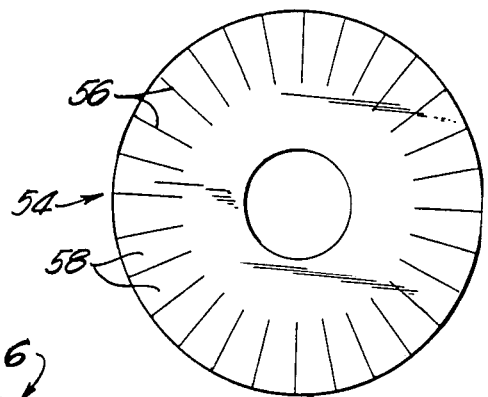
FIG. 15 is a view of the gasket forming a part of the piston assembly.

The flexible, thin disk is made in a substantially flat form as shown in FIG. 15 and assumes the shape shown in the drawings when assembled into the piston assembly.

The film disks 54 are more effective than conventional sealing rings and are less expensive. The effectiveness results from the fact that when the piston moves upwardly the flaps 58 tend to flatten out, and overlap and trap air between the flaps (FIG. 14). Thus, the flap arrangement makes an effective seal while substantially reducing conventional drag in that the flaps provide little resistance to the piston assembly movement.

As will be explained, the piston assembly moves upwardly upon inhalation. Gravity will cause the piston assembly to slowly fall to its lowest position due to the apertures 38 in the base 2 (FIG. 10) which permits the air to be expelled by pushing air through the apertures 38 in the base member 2.

In accordance with this invention, means is provided for permitting inhalation of air into human lungs wherein a relatively small proportion of air comes from within the device and a relatively large proportion of air comes from the atmosphere. This means is significant in that it permits the inhalation of a relatively large volume of air through use of a device which is quite compact in size. In other words, if all, or substantially most, of the inspired air came from within the device, a device having substantially greater cubic volume would be required.

In one embodiment of this invention approximately 4,000 ML of air can be inspired with a device which is only about ten (10") inches in height and having a chamber diameter of about two and one-fourth inches (2¼").

As can be seen in FIG. 1, the vertical column 4 has indicia thereon which indicates the amount of inspired air determined by the vertical position of the piston. As shown, the indicia ranges from 500 ML to 4,000 ML but obviously different indicia could be used.

Figure 5:
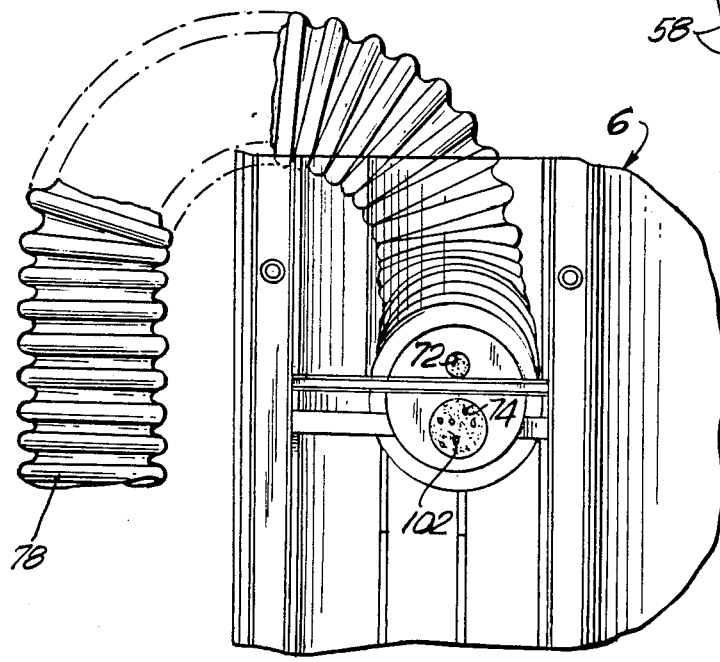
FIG. 5 is a partial view showing one of the features of the invention.

As embodied, the frame 8 includes horizontal supports 62, 64 extending between vertical legs 12 and 14 (FIG. 2). The hoizontal supports 62, 64 support a circular port assembly member 66. The port member includes grooves 68 on the front and back side of the port support 66. The circular port member 66 also includes a circular groove 70. The port member assembly includes a relatively small port 72 and a relatively large port 74. As will be explained, the ports 72, 74 are in communication with different chambers of the inhalation device. (FIG. 5)

Integral with one wall of the vertical column 6 is an inhalation port 76 to which is removably attached a flexible tube which can be made of polyethylene or ethylene vinyl acetate 78 having a mouthpiece 80 at its terminal end. The halves 9 and 11 of the columns 4 and 6 each includes planar sealing members 81 which fit in sealing relationship into the grooves 68. As in the case of the groove 68, the planar sealing member is in two sections. The inhalation port 76 includes a circular rim 82 which extends toward and into sealing engagement with the groove 70 in the port member (FIGS. 1 and 2)

A first chamber 91, FIG. 11, has thus been formed above the sealing member 81 which includes part of column 6 and all of column 4. A second chamber 93 is formed below the sealing shelf 81 which communicates with the atmosphere through the vertical openings 42.

Air is inspired from the first chamber 91 through port 72 and air is inspired from the atmosphere through port 74 and the second chamber 93.

In accordance with this invention, counterweight means is provided wherein at lower flow rates the counterweight offers greater resistance to the portion of air flowing through chamber 93 and port 74 thereby increasing the proportion of total air flowing through chamber 91 which moves the piston. At higher flow rates the counterweight offers less resistance to air flow. This change results in increased compensation where more air is needed at low flow rates due to the effect of leakage and friction and less compensation at higher flow rates where the effect of leakage and friction are less.

Figure 12:
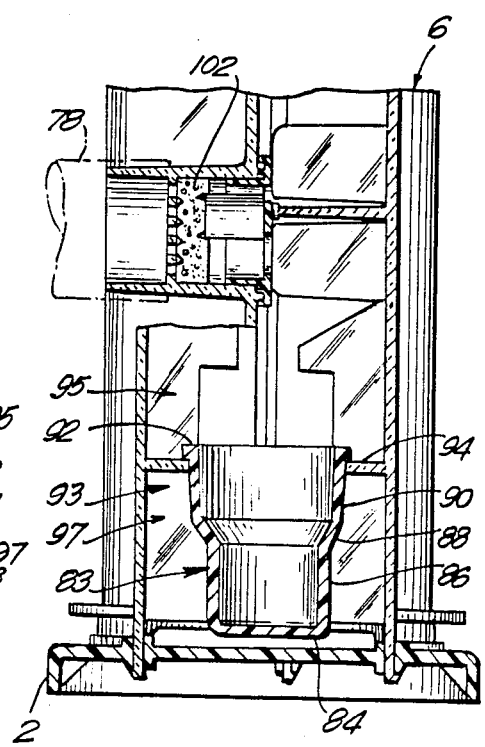
FIG. 12 is a cross-sectional view of the spirometer along line 12—12 indicated in FIG. 4.

As embodied, the counterweight means (FIG. 12) includes a cup shaped member 83, consisting of a bottom wall 84 connected to a cylindrical portion 86. Extending outwardly from the cylindrical portion 86 are the wall portions 88 which, in turn, merge with wall 90 which extends slightly outwardly. The wall 90 is not vertical but extends slightly outwardly from the vertical in an amount of 1 or 2 degrees. At the terminal end of the wall 90 is a radial outwardly extending circular flange 92. Extending radially inwardly from the interior wall of the vertical column 6 is a flange 94 on which the flange 92 rests when the counterweight means is in its position of rest. The second chamber 93 is divided into upper 95 and lower 97 chamber sections which are sealed from one another when the counterweight is in a position of rest.

As noted heretofore, the counterweight means provides resistance in the second chamber 93 to balance the resistance in the first chamber 91 caused by the resistance to movement encountered by the piston assembly in the vertical column 4.

The upper portion 95 of the second chamber is in communication with the inhalation tube through the large port 74. The lower portion 97 of the second chamber communicates with the atmosphere through vertical openings 42 (FIG. 6)

When air is removed from the upper portion of the second chamber through the mouthpiece 80, the counterweight means 83, due to reduced atmospheric pressure, causes the cup-shaped member to move upwardly thereby creating an opening between the flange 92 on the cup-shaped member and the flange 94.

As air is removed from the upper portion 95 of the second chamber, the cup-shaped counterweight member 83 moves upwardly thus breaking the seal between flanges 92 and 94 and permitting air from the atmosphere to pass into the lower portion 97 of the second chamber, through vertical openings 42, through the lower portion of the chamber 97 and into the upper portion of the chamber 95. As the flow rate increases, the cup moves further upwardly making the size of the opening between flanges 92 and 94 and wall 90 wider, thus reducing the resistance of the orifice between flanges 92 and 94 to the flow of air. It is for this reason that the wall 90 is slightly inclined outwardly. When the air flow rate is lower, the size of the orifice reduces thus increasing the resistance to air flow.

In this way the counterweight means adjusts to the resistance of the piston assembly. The effect of resistance on the piston assembly at high flow rates is less than the effect of resistance at low flow rates. With the counterweight means of the present invention, these effects are compensated for by the aforementioned structure.

It will be further understood that when the counterweight 83 rises a major portion of the inhaled air flows through the openings 42 and the port 74 to the mouthpiece 80.

The surface of the vertical column 6 also includes a small transparent window 98 which permits visual observation of the counterweight means and particularly the cup-like member 82. The window is formed by not frosting the window portion 98. This permits the technicians or other observers to view the cup member 83 to determine whether the flow rate is constant or erratic. This is significant in that it is generally considered desirable for the flow rate to be constant rather than erratic such as might occur if the air is suddenly gulped into the lungs.

The counterweight means also serves to indicate the rate of inhalation in that a high position of the cup-like member indicates a high rate of flow whereas a low position indicates a low rate of flow. Thus, the inhalation device of this invention indicates the volume of inhalation determined by the position of the piston assembly in the vertical column 4 which includes the volume indices as shown in FIG. 1 as well as rate of inhalation as indicated by the height of the counterweight cup-like member 83.

As noted previously, the ratio of the size of 72 and 74 is such that the opening 74 leading to the atmosphere is considerably greater than the size of the opening 72 leading to chamber 91 in which the piston assembly 83 is located.

The range can vary depending on the circumstances from 4:1 to 15:1. Preferably the ratio is about 9:1. With such an arrangement, if 400 ml is inhaled from chamber 93 and the port of opening ratio is 9:1, then 400 ml represents one-tenth (1/10) of the air inhaled and the total amount of air inhaled is 4,000 ML. Thus 400 ml comes from the first chamber 91 and 3,600 ML comes from the atmosphere for a total of 4,000 ML. Thus the relative size of the openings 72, 74 determine the indicia markings on the vertical column 4.

Positioned on one of the legs of the frame is a slidable pointer 100 which can be used to indicate the volume of inhalation. If desired, additional pointers can be used to compare past and present inhalation amounts.

In operation, the user inserts the mouthpiece 80 in the mouth and inhales. The removal of air through port 72 from the first chamber 91 caused the piston assembly 44 to rise within the vertical column 4. The height of the piston can be recorded by position of the height indicator 100 at the highest point of the piston assembly 44.

The air inhalation also causes the counterweight member to rise causing atmospheric air to be inhaled through the opening or port 74 in an amount dependent on the size ratio between openings 72 and 74.

When inhalation stops, the piston assembly will slowly fall to the bottom of vertical column 4.

In order to ensure that the inhaled air is substantially free of contamination a filter 102 can be positioned within the inhalation port.

The present invention is useful for therapy, building lung capacity for athletes, or for recuperation purposes and could also be used for entertainment purposes.

As noted earlier, the parts of the device of this invention can be made of a variety of plastics. Thus, for example, the vertical columns can be made of polycarbonate, polystyrene, or styrene-acrylonitrile. The base, pointer, counterweight and mouthpiece can be made of polyethylene or polypropylene. The outer frame can be made of ethylene vinyl acetate, polyethylene or polyurethane thermoplastic rubber. It will be understood, of course, that other and different material can be used for the above parts, if desired.

What is claimed is:

1. A piston assembly adapted to cooperate with a cylinder comprising:
   a. a cylindrical base member having a substantially flat surface and a vertical, circular outer surface in proximity to and parallel to said cylinder;
   b. a centrally located circular stud means extending at right angles from the substantially flat horizontal surface to said base member;
   c. a cylindrical top piston assembly part having an outer diameter substantially equal to the diameter of said base member and a hollow cylindrical part in fitting relationship with said stud means, a substantially flat surface extending from said stud and positioned in parallel relationship with said flat surface of said base member surface of said base member;
   d. inclined surfaces on said base and said top part extending at an acute angle between said cylindrical surfaces and said flat surfaces, such inclined surface being parallel.
   e. at least one thin, flexible, circular, film-like disk member having an outer diameter substantially greater than the diameter of said base member and said top piston assembly part, a circular aperature in the center thereof having a diameter greater than said stud member, said stud member being adapted to fit within said aperature;
   f. a plurality of substantially evenly spaced radial, inwardly extending slits in said film-like member forming a plurality of substantially equal film sections;
   g. means positioning at least one film-like disk member between said base member and said top piston assembly member so that said film-like member engages said substantially flat surfaces and extends downwardly adjacent to said inclined surfaces whereby said film sections overlap to trap air between the overlapping sections, a portion of said disk-like member adapted to engage vertical surface when the piston and cylinder are in operating position.

2. A piston assembly as defined in claim 1 having
   a. a circular intermediate member positioned between said base member and said top member having a diameter substantially equal to said base and said top member and having a circular opening therein adapted to fit over said stud member;
   b. said intermediate member having upper and lower substantially flat surfaces terminating in downwardly extending inclined surfaces parallel to said downwardly inclined surfaces on said base member and said top member;
   c. at least two of said film-like members, a first film-like member being positioned between said top piston assembly and said intermediate assembly, a second film-like member positioned between said intermediate assembly and said base member.

* * * * *